US00PP23584P2

(12) United States Plant Patent
Smutzer et al.

(10) Patent No.: US PP23,584 P2
(45) Date of Patent: May 7, 2013

(54) ***PIERIS* PLANT NAMED 'GREPRS'**

(50) Latin Name: *Pieris japonica*
Varietal Denomination: Greprs

(75) Inventors: Harry Smutzer, El Campo, TX (US); Mark Rainey, Needville, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 13/385,118

(22) Filed: Feb. 2, 2012

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette Para
(74) *Attorney, Agent, or Firm* — Penny J. Aguirre

(57) ABSTRACT

A new cultivar of *Pieris japonica* named 'Greprs' that is characterized by its high rate of propagation success and its healthy foliage and a vigorous growth habit in the southern regions of the U.S., its dense foliage with new spring foliage that emerges green in color with a light pink blush under cool temperatures in containers, its high degree of resistance to root rot and leaf spot, and its white flowers that emerge from white flower buds.

2 Drawing Sheets

Genus/species: *Pieris japonica.*
Varietal denomination: 'Greprs'.

BACKGROUND OF THE INVENTION

The present invention relates to a new and distinct cultivar of *Pieris japonica* and will be referred to hereafter by its cultivar name, 'Greprs'. 'Greprs' represents a new cultivar of *Pieris*, an evergreen shrub grown for landscape use.

The new *Pieris* arose as a whole plant mutation from seed grown from open pollination of 'Temple Bells' (not patented). The male parent is therefore unknown. 'Greprs' was selected as a single unique plant by one of the Inventors in El Campo, Tex. in August of 2008.

Asexual reproduction of the new cultivar was first accomplished by stem cuttings by one of the Inventors in El Campo, Tex. in April 2009. The characteristics of this cultivar have been determined to be stable and are reproduced true to type in successive generations.

SUMMARY OF THE INVENTION

The following traits have been repeatedly observed and represent the characteristics of the new *Pieris*. These attributes in combination distinguish 'Greprs' as unique and distinct from all other cultivars of *Pieris* known to the Inventors.

1. 'Greprs' exhibits a high rate of propagation success in the southern regions of the U.S. with successful rooting averaging 85 to 90% in trials. Rooting rates are typically low for plants of *Pieris japonica* when cuttings taken are taken from plants grown in hot climates.
2. 'Greprs' performs well in the hot, humid climates of the southern region of the U.S.; exhibiting healthy foliage and a vigorous growth habit. Plants of *Pieris japonica* typically struggle to thrive under these conditions.
3. 'Greprs' exhibits dense foliage with new spring foliage that emerges green in color with a variable light pink blush when grown in containers (more prevalent when grown in cool temperatures).

4. 'Greprs' exhibits a high degree of resistance to root rot and leaf spot.
5. 'Greprs' exhibits white flowers that emerge from white flower buds.

'Greprs' can be most closely compared to its female parent, 'Temple Bells'. 'Temple Bells' differs from 'Greprs' in having new foliage in spring that is flushed with apricot-bronze and deepening to reddish bronze before turning green, in having flower buds that are pinkish white in color, and in having less vigor, less resistance to leaf spot and root rot, and a lower rooting rate when grown in hot climates. 'Greprs' can also be compared to the cultivar 'Mountain Snow' (not patented), which is similar to 'Greprs' in having vigor when grown in hot climates and in having white flower buds. 'Mountain Snow' differs from 'Greprs' in having a more vigorous growth habit resulting in a more open and less dense plant habit, and in having new spring foliage that is bronze in color.

BRIEF DESCRIPTION OF THE DRAWING

The accompanying photographs were taken of a seven year-old plant of 'Greprs' as grown outdoors in a seven-gallon container in El Campo, Tex.

The photograph in FIG. 1 provides an overall view of 'Greprs' in bloom.

Figure 1:
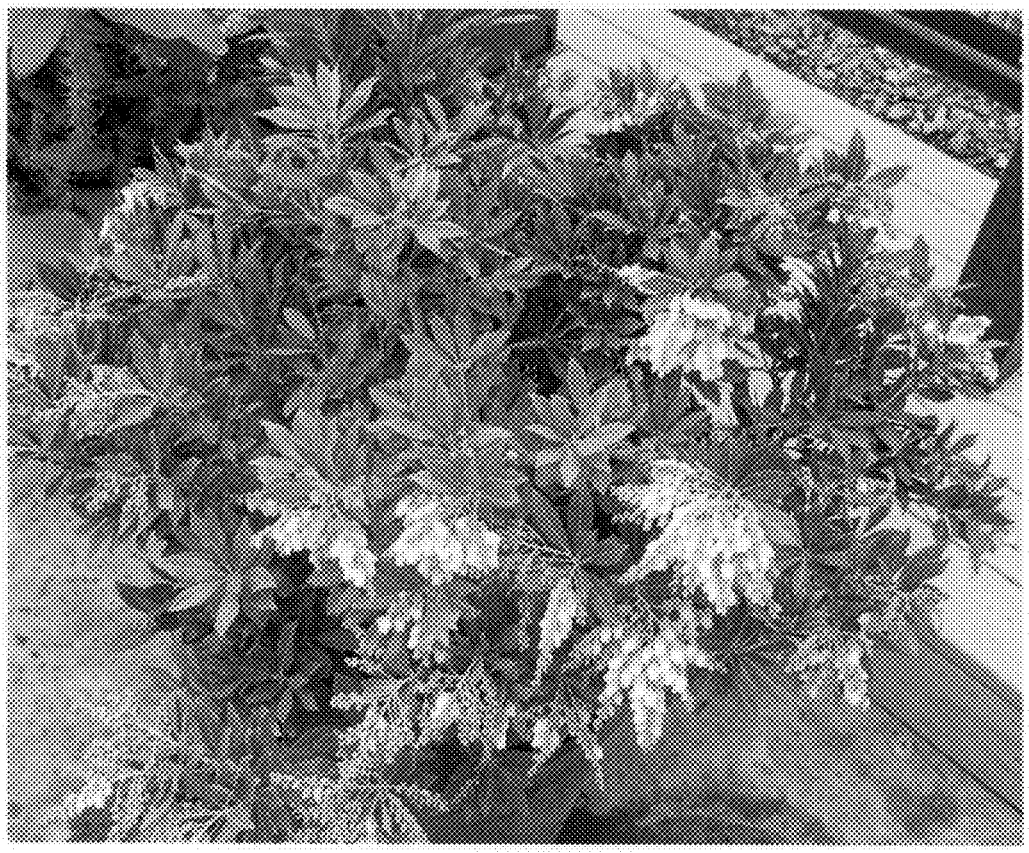
Figure 2:
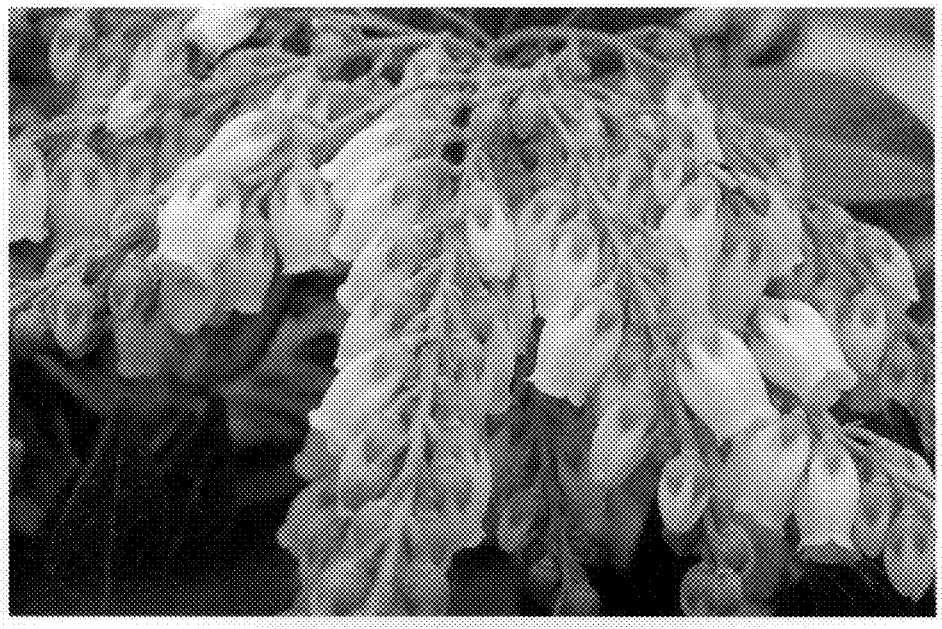

The photograph in FIG. 2 provides a close-up of the inflorescences of 'Greprs'.

Figure 3:
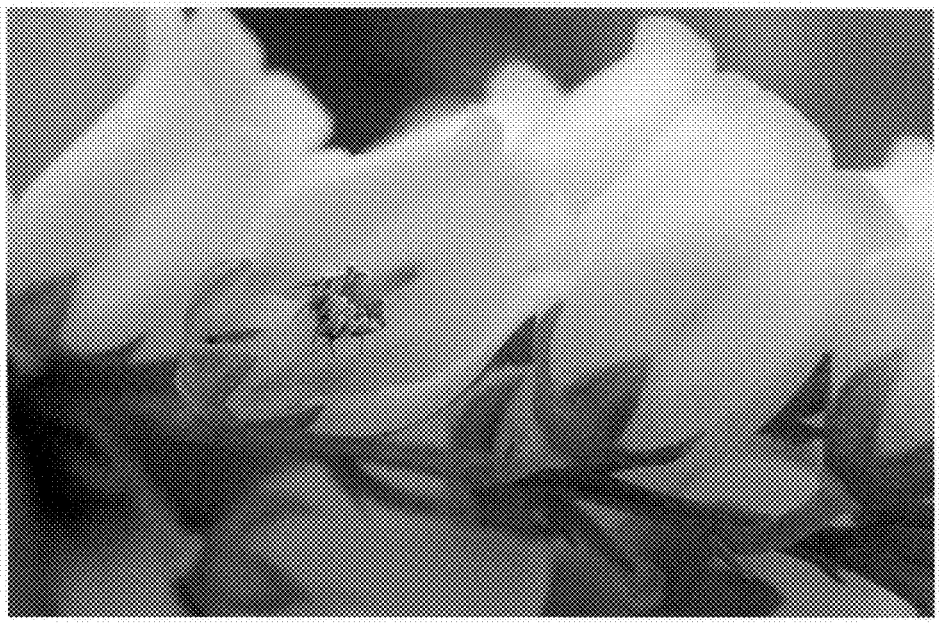

The photograph in FIG. 3 provides a close-up view of the flowers of 'Greprs'.

The colors in the photographs are as close as possible with the digital photography and printing techniques utilized and the color codes in the detailed botanical description accurately describe the colors of the new *Pieris.*

BOTANICAL DESCRIPTION OF THE PLANT

The following is a detailed description of three year-old plants of the new cultivar as grown outdoors in 3-gallon containers in El Campo, Tex. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant habit.*—Broadleaf evergreen shrub.

*Plant habit.*—Densely clean foliage, mounded.

*Blooming period.*—Mid February to mid April in southeastern Texas.

*Height and spread.*—An average of 40 cm in height and 50 cm in spread (3-gallon container), mature height and spread in the landscape as not been determined.

*Hardiness.*—Heat tolerance is at least U.S.D.A. Zone 8b, cold hardiness has not been determined.

*Environmental and cultural tolerance.*—Performs well in the heat and humidity of the southern U.S.

*Diseases resistance.*—Good resistance has been observed for root rot and leaf spot, both diseases are typically problematic for plants of *Pieris japonica* when grown in hot climates.

*Growth rate.*—Moderate, but more vigorous than is typical for most plants of *Pieris japonica* when grown in hot climates.

Branch description:

*Branch color.*—New growth; 144D and sparsely covered with vegetative buds about 1 mm in diameter and 177A in color, flush of 60B and irregularly streaked with 144D has been observed on sun exposed stems grown in containers under 50% shade cloth, mature wood; a blend of 177A and 177B.

*Branch shape.*—Oval.

*Branch size.*—Main stem; about 12 cm in length and 1 cm in width, lateral braches an average of 28 cm in length and 5 mm in width in center of branch.

*Branch surface.*—Glabrous and slightly ridged.

*Branching.*—Well branched; an average of 10 lateral branches each with an average 4 secondary branches.

Foliage description:

*Leaf shape.*—Oblanceolate.

*Leaf division.*—Simple.

*Leaf base.*—Cuneate.

*Leaf apex.*—Acuminate.

*Leaf venation.*—Pinnate, only midrib is conspicuous; 145B on upper surface, 145C on lower surface.

*Leaf margin.*—Entire with very apex serrated.

*Leaf attachment.*—Petiolate.

*Leaf arrangement.*—Spiral and whorled near terminus of branches.

*Leaf surface.*—Glabrous on upper surface and finely puberulent.

*Leaf texture.*—Leathery.

*Leaf size.*—An average of 6 cm and 2 cm in width.

*Leaf number.*—About 23 per branch 16 cm in length.

*Internode length.*—An average of 2 mm in whorls and 3 cm between whorls and on lower portion of branch.

*Leaf color.*—Young upper surface; 137A and flushed with 58D under cool growing conditions in containers, young lower surface; 144A with puberulent coating 138C, mature upper surface; 147A, mature lower surface; 147B.

*Petioles.*—About 6 mm in length and 2 mm in width, 146C in color, surface glabrous.

*Stipules.*—None.

*Leaf buds in leaf axils.*—1 to 2 mm in diameter and 177A in color.

Flower description:

*Inflorescence type.*—Branched racemes, up to 10 branches per inflorescence.

*Inflorescence size.*—Up to 10 cm in length and 12 cm in width.

*Inflorescence lastingness.*—3 to 4 weeks.

*Flower type.*—Closed campanulate, urn-shaped.

*Flower fragrance.*—Slight.

*Flower bud description.*—Buds are formed the previous season, ovate in shape with slightly rounded base and broadly ovate apex, about 4.5 mm in length and 4 mm in width, a blend of 138A and 138B in color, prior to flower opening; about 1.2 cm in length and 8 mm in width, base is a blend of 144A and 144B in color with apex whiter than NN155D.

*Flower quantity.*—About 30 flowers per raceme branch, an average of 200 per inflorescence.

*Flower size.*—About 1.6 cm in depth and 1 cm diameter.

*Rachis.*—Branches are about 7 cm in length and 1.5 mm in width, 144C in color.

*Pedicels.*—About 4.5 mm in length and 1 mm in diameter, 144C in color.

*Petal description.*—5, oblong in shape and fused with very apex un-fused, margin is entire, apex of un-fused portion rounded, lower and upper surface is glabrous, base fused, color whiter than NN155D, about 4.5 cm in length and 4 mm in width.

*Calyx.*—Open campanulate, Average of 4 mm in length and 8 mm in diameter.

*Sepal description.*—5, ovate in shape, margin is entire, apex is acute, surface is glabrous on upper and lower surface, an average of 4 mm in length and 2 mm in width, color is a blend of 144A and 144B.

Reproductive organs:

*Gynoecium.*—1 Pistil about 5 mm in length, stigma is globular in shape and 145A in color, style is about 4.9 mm in length and 145C in color, ovary is 145A in color.

*Androecium.*—5, anthers are oblong in shape, about 2 mm in length and 161A in color with 2 hairs extending from anthers about 0.5 mm in length and 177B in color, pollen is abundant and NN155C in color.

*Fruit and seed.*—Five-valved capsules persist throughout the year on the fruiting stalks, ornamentally insignificant, about 1 mm in width and length and 177A in color, seed was not discernable.

It is claimed:

1. A new and distinct cultivar of *Pieris* plant named 'Greprs' substantially as herein illustrated and described.

* * * * *